United States Patent [19]
Peet et al.

[11] Patent Number: 5,734,052
[45] Date of Patent: Mar. 31, 1998

[54] 8-SUBSTITUTED XANTHINES AS SELECTIVE ADENOSINE RECEPTOR AGENTS

[75] Inventors: Norton P. Peet, Cincinnati; Nelsen L. Lentz, West Chester, both of Ohio

[73] Assignee: Merrell Pharmaceuticals Inc., Cincinnati, Ohio

[21] Appl. No.: 553,253
[22] PCT Filed: Apr. 13, 1994
[86] PCT No.: PCT/US94/04038
    § 371 Date: Oct. 26, 1995
    § 102(e) Date: Oct. 26, 1995
[87] PCT Pub. No.: WO94/26744
    PCT Pub. Date: Nov. 24, 1994

Related U.S. Application Data

[63] Continuation of Ser. No. 58,523, May 6, 1993, abandoned.
[51] Int. Cl.$^6$ .................... C07D 473/06; C07D 473/08; A61K 31/52
[52] U.S. Cl. ............... 544/273; 544/267; 544/272
[58] Field of Search .................... 544/267, 272, 544/273

[56] References Cited

U.S. PATENT DOCUMENTS

| | | | |
|---|---|---|---|
| 4,772,607 | 9/1988 | Badger et al. | 514/263 |
| 5,047,534 | 9/1991 | Peet et al. | 544/267 |
| 5,208,240 | 5/1993 | Peet et al. | 514/263 |
| 5,641,784 | 6/1997 | Kufner-Muhl et al. | 544/272 |

FOREIGN PATENT DOCUMENTS

| | | |
|---|---|---|
| 0499175 | 10/1991 | European Pat. Off. . |
| 1435916 | 5/1976 | United Kingdom . |
| 9200297 | 1/1992 | WIPO . |

OTHER PUBLICATIONS

Baziard–Mouysset, Chem Abs 123, 111738 (1995).
Peet et al., J. Med. Chem., vol. 36, No. 25, pp. 4015–4020 (1993).
Erickson et al., J. Med. Chem. vol. 34, No. 4, pp. 1431–1435 (1991).

Primary Examiner—Mark L. Berch
Attorney, Agent, or Firm—Nelson L. Lentz

[57] ABSTRACT

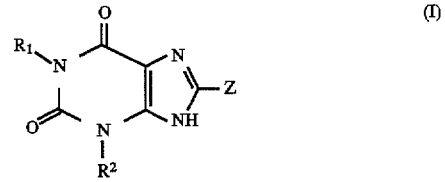

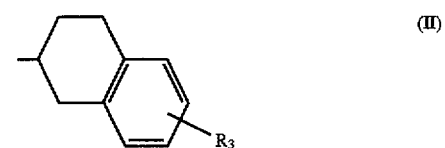

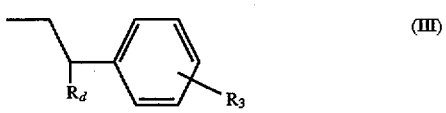

Xanthine derivatives having general structure (I) including the (R) and (S) enantiomers and racemic mixtures thereof, and the pharmaceutically acceptable salts thereof, wherein $R_1$ and $R_2$ are each independently ($C_1$–$C_4$)lower alkyl or ($C_2$–$C_4$)lower alkenyl, Z is (II) or (III) or (IV) wherein $R_3$ is hydrogen, ($C_1$–$C_3$)lower alkyl, nitro, amino, hydroxy, fluoro, bromo or chloro, $R_4$ is ($C_1$–$C_4$)lower alkyl and n is 1 or 2 which act selectively at adenosine receptors and which act in general as adenosine antagonists are disclosed. From in vitro studies it is known that specific physiological effects can be distinguished as a result of this selectivity and that adenosine receptor activity in vitro correlates with adenosine receptor activity in vivo. Pharmaceutical preparations of the subject compounds can be prepared on the basis of the selective binding activity of the compounds disclosed herein which will enhance certain physiological effects while minimizing others, such as descreasing blood pressure without descreasing heart rate.

1 Claim, No Drawings

8-SUBSTITUTED XANTHINES AS SELECTIVE ADENOSINE RECEPTOR AGENTS

The present application has an effective international filing date of Apr. 13, 1994 as application PCT/US94/04038 which designated the U.S. and entered the U.S. national phase on Nov. 1, 1995 under 35 USC 371 and was assigned Ser. No. 08/553,253, which is a continuation of application Ser. No. 08/058,523 filed on May 6, 1993, now abandoned.

FIELD OF THE INVENTION

The present invention relates to a group of compounds which are xanthine derivatives and which act selectively at adenosine receptors.

BACKGROUND OF THE INVENTION

The profound hypotensive, sedative, antispasmodic, and vasodilatory actions of adenosine were first recognized over 50 years ago. Subsequently, the number of biological roles proposed for adenosine have increased considerably. The adenosine receptors appear linked in many cells to adenylate cyclase. A variety of adenosine analogues have been introduced in recent years for the study of these receptor functions. Alkylxanthines, such as caffeine and theophylline, are the best known antagonists of adenosine receptors.

Adenosine perhaps represents a general regulatory substance, since no particular cell type or tissue appears uniquely responsible for its formation. In this regard, adenosine is unlike various endocrine hormones. Nor is there any evidence for storage and release of adenosine from nerve or other cells. Thus, adenosine is unlike various neurotransmitter substances.

Adenosine might be compared as a physiological regulator to the prostaglandins. In both cases the enzymes involved in the metabolic formation are ubiquitous and appear to be responsive to alterations in the physiological state of the cell. Receptors for adenosine, like those for prostaglandins, are proving to be very widespread. Finally, both prostaglandins and adenosine appear to be involved with the regulation of functions involving calcium ions. Prostaglandins, of course, derive from membrane precursors, while adenosine derives from cytosolic precursors.

Although adenosine can affect a variety of physiological functions, particular attention has been directed over the years toward actions which might lead to clinical applications. Preeminent has been the cardiovascular effects of adenosine which lead to vasodilation and hypotension but which also lead to cardiac depression. The antilipolytic, antithrombotic and antispasmodic actions of adenosine have also received some attention. Adenosine stimulates steroidogenesis in adrenal cells, again probably via activation of adenylate cyclase. Adenosine has inhibitory effects on neurotransmission and on spontaneous activity of central neurons. Finally, the bronchoconstrictor action of adenosine and its antagonism by xanthines represents an important area of research.

It has now been recognized that there are not one but at least two classes of extracellular receptors involved in the action of adenosine. One of these has a high affinity for adenosine and at least in some cells couples to adenylate cyclase in an inhibitory manner. These have been termed by some as the A-1 receptors. The other class of receptors has a lower affinity for adenosine and in many cell types couples to adenylate cyclase in a stimulatory manner. These have been termed the A-2 receptors.

Characterization of the adenosine receptors has now been possible with a variety of structural analogues. Adenosine analogues resistant to metabolism or uptake mechanisms have become available. These are particularly valuable, since their apparent potencies will be less affected by metabolic removal from the effector system. The adenosine analogues exhibit differing rank orders of potencies at A-1 and A-2 adenosine receptors, providing a simple method of categorizing a physiological response with respect to the nature of the adenosine receptor. The blockade of adenosine receptors (antagonism) provides another method of categorizing a response with respect to the involvement of adenosine receptors. It should be noted that the development of antagonists specific to A-1 or A-2 adenosine receptors would represent a major breakthrough in this research field and in the preparation of adenosine receptor selective pharmacological agents having specific physiological effects in animals.

SUMMARY OF THE INVENTION

The present invention relates to compounds having the following general structures:

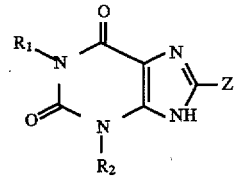

including the (R) and (S) enantiomers and racemic mixtures thereof, and the pharmaceutically acceptable salts thereof, wherein $R_1$ and $R_2$ are each independently $(C_1-C_4)$ lower alkyl or $(C_2-C_4)$ lower alkenyl, Z is:

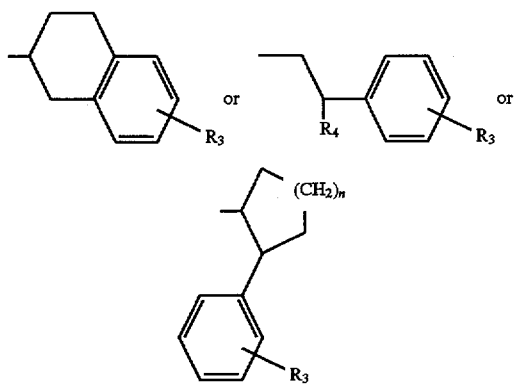

wherein $R_3$ is hydrogen, $(C_1-C_3)$ lower alkyl, nitro, amino, hydroxy, fluoro, bromo or chloro, $R_4$ is $(C_1-C_4)$ lower alkyl and n is 1 or 2.

As used in this application the term $(C_1-C_3)$ lower alkyl refers to methyl, ethyl, n-propyl, or isopropyl. Also, as used in this application the term $(C_1-C_4)$ lower alkyl refers to methyl, ethyl, n-propyl, isopropyl, n-butyl, isobutyl, sec-butyl or tert-butyl.

In addition as used in this application the term $(C_2-C_4)$ lower alkenyl refers to ethenyl, propenyl, isopropenyl, butenyl, isobutenyl, etc.

Also, as used in this application, the substituent represented by $R_3$ may be at any position from 2–6 around the phenyl ring or 5–8 around the 1,2,3,4-tetrahydronaphthyl ring. There may be up to three such independent substitutions around the ring wherein the substituent is other than hydrogen.

DETAILED DESCRIPTION OF THE INVENTION

In general, compounds according to the invention can be made by following the procedures described in detail in Schemes I and II below.

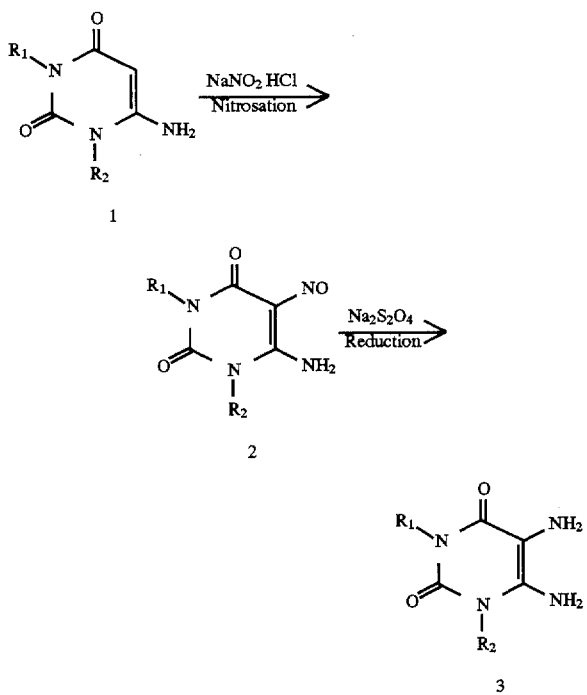

Scheme I

1

2

3

An appropriately alkyl substituted starting compound 1, 6-amino-2,4(1H,3H)-pyrimidinedione, wherein $R_1$ and $R_2$ are defined as above.

The 6-amino-2,4(1H,3H)-pyrimidinedione is suspended in water with 20% acetic acid. Sodium nitrite (1.5 equivalents) in water is added in portions while keeping the solution mildly acidic with concentrated hydrochloric acid. The suspension is allowed to stir for several hours. It is then filtered, rinsed with water and dried under vacuum to yield the purple colored, alkyl substituted 6-amino-5-nitroso-2, 4(1H,3H)-pyrimidinedione (2).

The alkyl substituted 6-amino-5-nitroso-2,4(1H,3 H)-pyrimidinedione is then suspended in water, made alkaline with 50% ammonium hydroxide (pH≈11) and treated with excess sodium dithionite until the purple color fades. The reaction is then extracted with chloroform. The organic extracts are combined and dried over anhydrous magnesium sulfate, filtered and concentrated under vacuum. The residue is purified by flash chromatography (5% to 10% methanol in chloroform). This material is then recrystalized from 10% isopropanol/hexane to yield the alkyl substituted 5,6-diamino-2,4(1H,3H)-pyrimidinedione (3). See J. W. Daly, *J. Med. Chem.*, 28, 487, 1985.

Compound 3 from Scheme I is then reacted as shown in Scheme II. All substituents are as previously defined.

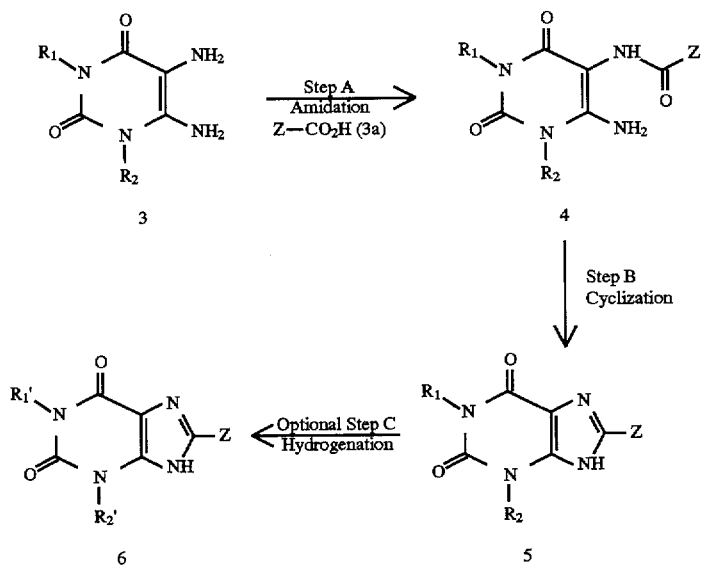

Scheme II

3

4

5

6

$R_1'$ and $R_2'$ = $(C_2-C_4)$ lower alkyl

In Scheme II, step A the alkyl substituted 5,6-diamino-2,4(1H,3H)-pyrimidinedione (3) is subjected to an amidation reaction with an appropriately substituted acid defined by structure (3a) under conditions well known in the art to provide the appropriately substituted amide described by structure (4).

For example, an appropriately substituted acid (3a) is dissolved in a suitable organic solvent, such as tetrahydrofuran. Examples of appropriately substituted acids (3a) are 3-phenylbutyric acid, 1,2,3,4-tetrahydro-2-naphthoic acid and trans-2-phenylcyclopentanecarboxylic acid. One equivalent of N-methylmorpholine is added to the solution which is then cooled to −20° C. One equivalent of isobutyl chloroformate is added and the reaction is allowed to stir for approximately 20 minutes. One equivalent of the alkyl substituted 5,6-diamino-2,4(1H,3H)-pyrimidinedione (3) in a suitable organic solvent, such as dimethylformamide is added and the reaction is allowed to stir at −20° C. for approximately 3 hours. The reaction is then diluted with a suitable organic solvent, such as diethyl ether, rinsed with saturated sodium bicarbonate, 50% or saturated sodium chloride, dried over anhydrous magnesium sulfate, filtered and concentrated under vacuum to provide the appropriately substituted amide (4).

In Scheme II, step B the amide (4) is subjected to a cyclization reaction under conditions well known in the art as described by Peet et al., *J. Med. Chem.*, 33, 3127, (1990), to provide the appropriately substituted 1,3-dialkyl-8-substituted xanthine described by structure (5).

For example, the appropriately substituted amide (4) is dissolved in a suitable organic solvent, such as ethanol and the solution is treated with a 10 to 20% aqueous solution of a suitable base, such as potassium hydroxide. The reaction is then heated from about 40° to 60° C. for about 1 to 6 hours. The reaction is then cooled and acidified with a suitable acid, such as hydrochloric acid. The crude product is extracted from the aqueous medium with a suitable organic solvent, such as diethyl ether. The combined organic extracts are rinsed with water, saturated sodium chloride solution, dried over anhydrous magnesium sulfate, filtered and concentrated. Alternatively, precipitated crude material may be isolated by filtration of the acidified aqueous medium described above. The residue or collected precipitate is then purified by techniques well known in the art, such as radial chromatography, utilizing a suitable eluant such as ethyl acetate/hexane to provide the appropriately substituted 1,3-dialkyl-8-substituted xanthine (5).

In Scheme II, optional step C the 1,3-dialkyl-8-substituted xanthine (5) is hydrogenated when the 1,3-dialkyl substituents $R_1$ and $R_2$ are ($C_2$–$C_4$) lower alkenyl to provide the appropriately substituted 1,3-dialkyl-8-substituted xanthine (6) wherein the 1,3-dialkyl substituents $R_1'$ and $R_2'$ are ($C_2$–$C_4$) lower alkyl.

For example, the appropriately substituted 1,3-dialkyl-8-substituted xanthine (5), such as 1,3-diallyl-8-substituted xanthine is dissolved in a suitable organic solvent, such as methanol. A catalytic amount of a suitable hydrogenation catalyst is added, such as palladium on carbon and the reaction is placed under an atmosphere of hydrogen with stirring for approximately 30 minutes to 4 hours. The reaction is then purged with an inert gas, such as nitrogen, filtered and concentrated under vacuum. The residue is then purified by techniques well-known in the art, such as radial chromatography utilizing a suitable eluant, such as ethyl acetate/hexane to provide the appropriately substituted 1,3-dialkyl-8-substituted xanthine (6).

The following list illustrates compounds prepared according to the present invention:

8-(2-phenylpropyl)-1,3-dipropyl-3,9-dihydropurine-2,6-dione;

1,3-dipropyl-8-(1,2,3,4-tetrahydronaphthalen-2-yl)-3,9-dihydropurine-2,6-dione; and 8-(trans-2-phenylcyclopentyl)-1,3-dipropyl-3,9-dihydropurine-2,6-dione.

Therapeutic Utility Of Selective Adenosine Receptor Agents

The table below shows in more detail the potential therapeutic utility of selective adenosine receptor agents in accordance with the present invention:

| Area | Effect | Receptor Correlate |
|---|---|---|
| Cardiovascular | cardiotonic | A-1 antagonism |
| Cardiovascular | control tachycardia | A-1 agonism |
| Cardiovascular | increase coronary blood flow | A-2 agonism |
| Cardiovascular | vasodilation | A-2 (atypical) agonism |
| Pulmonary | bronchodilation | A-1 antagonism |
| Pulmonary | mediation of autocoid release from mast cells, basophils | novel adenosine receptor interaction on cell surface |
| Pulmonary | stimulate respiration; treat paradoxical ventilatory response (infants) | Ado antagonism |
| Renal | inhibit renin release | A-1 agonism |
| Central Nervous System | aid in opiate withdrawal | Ado agonism |
| Central Nervous System | analgesic | A-1 agonism |
| Central Nervous System | anticonvulsant | A-1 agonism |
| Central Nervous System | antidepressant | A-1 agonism |
| Central Nervous System | antipsychotic | Ado agonism |
| Central Nervous System | anxiolytic | agonism |
| Central Nervous System | inhibition of self-mutilation behavior (Lesch-Nyhan syndrome) | Ado agonism |
| Central Nervous System | sedative | A-2 agonism |

In the cardiovascular, pulmonary and renal system targets, designed compounds which are identified by receptor binding studies can be evaluated in functional in vivo tests which are directly indicative of the human physiological response. A good description of the pharmacology and functional significance of purine receptors is presented by M. Williams, *Ann. Rev. Pharmacol. Toxicol.*, 27, 31 (1987). In a section entitled "Therapeutic Targeting of Adenosine Receptor Modulators" it is stated that "adenosine agonists may be effective as antihypertensive agents, in the treatment of opiate withdrawal, as modulators of immune competence and renin release, as antipsychotics and as hypnotics. Conversely, antagonists may be useful as central stimulants, inotropics, cardiotonics, antistress agents, antiasthmatics, and in the treatment of respiratory disorders." The smorgasbord of activities displayed by adenosine receptor agents underscores their great potential utility for therapy and the need for specific agents.

Adenosine exerts its various biological effects via action on cell-surface receptors. These adenosine receptors are of two types: A-1 and A-2. The A-1 receptors are operationally defined as those receptors at which several $N^6$-substituted adenosine analogs such as R-phenylisopropyladenosine (R-PIA) and cycloadenosine (CHA) are more potent than 2-chloroadenosine and N-5'-ethylcarboxamidoadenosine (NECA). At A-2 receptors the order of potency is instead NECA>2-chloroadenosine>R-PIA>CHA.

As illustrated in the table above, adenosine receptors govern a variety of physiological functions. The two major classes of adenosine receptors have already been defined. These are the A-1 adenosine receptor, which is inhibitory to adenylate cyclase, and the A-2 adenosine receptor, which is stimulatory to adenylate cyclase. The A-1 receptor has a higher affinity for adenosine and adenosine analogs than the A-2 receptor. The physiological effects of adenosine and adenosine analogs are complicated by the fact that nonselective adenosine receptor agents first bind the rather ubiquitous low-affinity A-2 receptors, then as the dose is increased, the high-affinity A-2 receptors are bound, and finally, at much higher doses, the very high-affinity A-1 adenosine receptors are bound. See J. W. Daly, et al., *Subclasses of Adenosine Receptors in the Central Nervous System: Interaction with Caffeine and Related Methylxanthines, Cellular and Molecular Neurobiology*, 3(1), 69–80 (1983).

In general, the physiological effects of adenosine are mediated by either the stimulation or the inhibition of adenylate cyclase. Activation of adenylate cyclase increases the intracellular concentration of cyclic AMP, which, in general, is recognized as an intracellular second messenger. The effects of adenosine analogs can therefore be measured by either the ability to increase or the ability to antagonize the increase in the cyclic AMP in cultured cell lines. Two important cell lines in this regard are VA 13 (WI-38 VA 13 2RA), SV-40 transformed WI 38 human fetal lung fibroblasts, which are known to carry the A-2 subtype of adenosine receptor, and fat cells, which are known to carry the A-1 subtype of adenosine receptor. See R. F. Bruns, *Adenosine Antagonism by Purines, Pteridines and Benzopteridines in Human Fibroblasts, Chemical Pharmacology*, 30, 325–33, (1981).

It is well known from in vitro studies that the carboxylic acid congener of 8-phenyl-1,3-dipropyl-xanthine (XCC) is adenosine receptor nonselective, with a Ki at the A-1 receptors in brain membranes of 58±3 nM and a Ki at the A-2 receptors of the brain slice assay of 34±13 nM. The amino congener of 8-phenyl-1,3-dipropyl-xanthine (XAC), on the other hand, has a 40-fold higher affinity for A-1 adenosine receptors, with a Ki of 1.2±0.5 nM, as compared with a Ki at the A-2 receptors of the brain slice assay of 49±17 nM. In addition, XAC is much more potent in antagonizing the effects of adenosine analogs on heart rate than on blood pressure. Since it is generally known that the adenosine analog-induced effects on the heart seem to be mediated via A-1 receptors and those on blood pressure via A-2 receptors, the selectivity of XAC under in vivo conditions suggests that adenosine receptor activity in vitro correlates with adenosine receptor activity in vivo and that specific physiological effects can be distinguished as a result of this selectivity. See B. B. Fredholm, K. A. Jacobsen, B. Jonzon, K. L. Kirk, Y. O. Li, and J. W. Daly, *Evidence That a Novel 8-Phenyl-Substituted Xanthine Derivative is a Cardioselective Adenosine Receptor Antagonist In Vivo, Journal of Cardiovascular Pharmacology*, 9, 396–400, (1987), and also K. A. Jacobsen, K. L. Kirk, J. W. Daly, B. Jonzon, Y. O. Li, and B. B. Fredholm, *Novel 8-Phenyl-Substituted Xanthine Derivative Is Selective Antagonist At Adenosine Receptors In Vivo, Acta Physiol. Scand.*, 341–42, (1985).

It is also known that adenosine produces a marked decrease in blood pressure. This blood pressure reduction is probably dependent upon an A-2 receptor-mediated decrease in peripheral resistance. Adenosine analogs are also able to decrease heart rate. This effect is probably mediated via adenosine receptors of the A-1 subtype.

Thus, it is readily apparent that the pharmacological administration of the adenosine receptor selective adenosine analogs disclosed herein will result in selective binding to either the A-2 or the A-1 receptor, which will, in turn, selectively result in either a decrease in blood pressure or a decrease in heart rate, for example, thereby decoupling these physiological effects in vivo. The selection of such adenosine receptor selective agents can be determined by the methods described in further detail below.

Test For Affinity For Brain Adenosine A-2 Receptors

The test described below was used to determine the potency of test compounds to compete with the ligand [3H]5'-N-ethyl-carboxamidoadenosine (NECA) for the adenosine A-2 receptors prepared from animal brain membranes. See also R. R. Bruns, G. H. Lu, and T. A. Pugsley, *Characterization of the A-2 Adenosine Receptor Labeled by [3H]NECA in Rat Striatal Membranes, Mol. Pharmacol.*, 29, 331–346, (1986). Young male rats (C–D strain), obtained from Charles River, are killed by decapitation and the brain was removed. Membranes for ligand binding are isolated from rat brain striatum. The tissue is homogenized in 20 vol ice-cold 50 mM Tris-HCl buffer (pH 7.7) using a polytron (setting for 6 to 20 seconds). The homogenate is centrifuged at 50,000×g for 10 minutes at 4° C. The pellet is again homogenized in a polytron in 20 vol of buffer, and centrifuged as before. The pellet is finally resuspended in 40 vol of 50 mM Tris-HCl (pH 7.7) per gram of original wet weight of tissue.

Incubation tubes, in triplicate, receive 100 µl of [3H] NECA (94 nM in the assay), 100 µl of 1 µM cyclohexyladenosine (CHA), 100 µl of 100 mM $MgCl_2$, 100 µl of 1 IU/ml adenosine deaminase, 100 µl of test compounds at various concentrations over the range of $10^{-10}$M to $10^{-4}$M diluted with assay buffer (50 mM Tris-HCl, pH 7.7) and 0.2 µl of membrane suspension (5 mg wet weight), in a final volume of 1 ml of 50 mM Tris-HCl, pH 7.7. Incubations are carried out at 25° C. for 60 minutes. Each tube is filtered through GF/B glass fiber filters using a vacuum. The filters are rinsed two times with 5 ml of the ice-cold buffer. The membranes on the filters are transferred to scintillation vials to which 8 ml of Omnifluor with 5% Protosol is added. The filters are counted by liquid scintillation spectrometry.

Specific binding of [3H]NECA is measured as the excess over blanks run in the presence of 100 µM 2-chloroadenosine. Total membrane-bound radioactivity is about 2.5% of that added to the test tubes. Since this condition limits total binding to less than 10% of the radioactivity, the concentration of free ligand does not change appreciably during the binding assay. Specific binding to membranes is about 50% of the total bound. Protein content of the membrane suspension is determined by the method of O. H. Lowry, N. J. Rosebrough, A. L. Farr and R. J. Randall, *Protein Measurements With Folin Phenol Reagent, J. Biol. Chem.*, 193, 265–275 (1951).

Displacement of [3H]NECA binding of 15% or more by a test compound is indicative of affinity for the adenosine A-2 site. The molar concentration of a compound which causes 50% inhibition of the binding of ligand is the $IC_{50}$.

A value in the range of 100–1000 nM would indicate a highly potent compound.

Test For Affinity For Brain Adenosine A-1 Receptor Binding Sites

The test described below is used to determine the potency of test compounds to compete with the ligand [3H]cycloadenosine for the Adenosine A-1 receptor prepared from rat brain membranes. Male Sprague-Dawley rats are sacrificed by decapitation and the membranes are isolated from whole animal brains. See R. Goodman, M. Cooper, M. Gavish, and S. Synder, *Guanine Nucleotide and Cation Regulation of the Binding of [3H]Diethylphenylxanthine to Adenosine A-1 Receptors in Brain Membrane, Molecular Pharmacology*, 21, 329–335, (1982).

Membranes are homogenized (using polytron setting 7 for 10 seconds) in 25 volumes of ice-cold 50 mM Tris-HCl buffer, pH 7.7. The homogenate is centrifuged at 19,000 rpm for 10 minutes at 4° C. The pellet is washed by resuspending in 25 volumes of buffer with 2 IU of adenosine deaminase per ml and incubated 30 minutes at 37° C. The homogenate is centrifuged again. The final pellet is resuspended in 25 volumes of ice-cold buffer.

The incubation tubes, in triplicate, receive 100 µl of [3H]cyclohexyladenosine, 0.8 nM in the assay, 200 µl of test compounds at various concentrations over the range of $10^{-10}$M to $10^{-6}$M diluted with 50 nM Tris-HCl buffer (pH 7.7), 0.2 ml of membrane suspension (8 mg wet weight) and in a final volume of 2 ml with Tris buffer. Incubations are carried out at 25° C. for 2 hours and each one is terminated within 10 seconds by filtration through a GF/B glass fiber filter using a vacuum. The membranes on the filters are transferred to scintillation vials. The filters are counted by liquid scintillation spectrometry in 8 ml of Omniflour containing 5% Protosol.

Specific binding of [3H]cycloadenosine is measured as the excess over blanks taken in the presence of $10^{-5}$M 2-chloroadenosine. Total membrane-bound radioactivity is about 5% of that added to the test tubes. Specific binding to membranes is about 90% of the total bound. Protein content of the membrane suspension is determined by the method of Lowry, et al., Id., 265.

Displacement of [3H]cyclohexyladenosine binding of 15% or more by a test compound is indicative of affinity for the adenosine binding site.

Adenosine Receptor Binding Affinity Values Obtained Using The Above Described Test Procedures The following is a table showing the adenosine receptor binding affinities for several compounds.

| Adenosine Receptor Binding Affinity | | | |
|---|---|---|---|
| | $A_1 K_i$ | $A_2 K_i$ | $A_2/A_1$ |
| 8-(2-phenylpropyl)-1,3-dipropyl-3,9-dihydropurine-2,6-dione | 94.3 nm | 1740 nm | 18 |
| 1,3-dipropyl-8-(1,2,3,4-tetrahydronaphthalen-2-yl)-3,9-dihydropurine-2,6-dione. | 94.6 nm | 10300 nm | 108 |

-continued

| Adenosine Receptor Binding Affinity | | | |
|---|---|---|---|
| | $A_1 K_i$ | $A_2 K_i$ | $A_2/A_1$ |
| 8-(trans-2-phenylcyclopentyl)-1,3-dipropyl-3,9-dihydropurine-2,6-dione | 164.3 nm | 2720 nm | 10 |

The nucleotide guanosine triphosphate (GTP) has been shown to differentially affect the binding of agonists and antagonists to a variety of neurotransmitter receptors. In general, guanine nucleotides lower the affinity of agonists for receptors without a concomitant decrease in antagonist affinity. Accordingly, GTP has been shown to decrease the potency of agonists but not antagonists as inhibitors of the binding of the adenosine antagonist [3H]3-diethyl-8-phenylxanthine. In general, GTP greatly reduces the potency of purine agonists, but not antagonists as inhibitors of [3H]-phenylisopropyl adenosine binding and is, therefore, an effective agent for distinguishing between agonists and antagonists. See L. P. Davies, S. C. Chow, J. H. Skerritt, D. J. Brown and G. A. R. Johnston, *Pyrazolo [3,4-d] Pyrimidines as Adenosine Antagonists, Life Sciences*, 34, 2117–28, (1984).

Pharmaceutical Preparations of the Adenosine Receptor Agents

The preferred route of administration is oral administration. For oral administration the compounds can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the breakup and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the esthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The compounds of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly (ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agents and other pharmaceutically adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, and alkyl pyridinium halides; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-β-aminopropionates, and 2-alkylimidazoline quaternary ammonium salts, as well as mixtures. Alternatively, the compounds of this invention can be administered by aerosolization with a suitable carrier directly into the nasal passages, or by the administration of droplets of a solution of the compounds of this invention, in an appropriate solvent, directly into the nasal passages.

The parenteral compositions of this invention will typically contain from about 0.5 to about 25% by weight of the active ingredient in solution. Preservatives and buffers may also be used advantageously. In order to minimize or eliminate irritation at the site of injection, such compositions may contain a nonionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The exact amount of the compound or compounds to be employed, i.e., the amount of the subject compound or compounds sufficient to provide the desired effect, depends on various factors such as the compound employed; type of administration; the size, age and species of animal; the route, time and frequency of administration; and, the physiological effect desired. In particular cases, the amount to be administered can be ascertained by conventional range finding techniques.

The compounds are preferably administered in the form of a composition comprising the compound in admixture with a pharmaceutically acceptable carrier, i.e., a carrier which is chemically inert to the active compound and which has no detrimental side effects or toxicity under the conditions of use. Such compositions can contain from about 0.1 μg or less to 500 mg of the active compound per ml of carrier to about 99% by weight of the active compound in combination with a pharmaceutically-acceptable carrier.

The compounds may also be incorporated into any inert carrier so that they may be utilized in routine serum assays, blood levels, urine levels, etc., according to techniques well known in the art.

The compositions can be in solid forms, such as tablets, capsules, granulations, feed mixes, feed supplements and concentrates, powders, granules or the like; as well as liquid forms such as sterile injectable suspensions, orally administered suspensions or solutions. The pharmaceutically acceptable carriers can include excipients such as surface active dispersing agents, suspending agents, tableting binders, lubricants, flavors and colorants. Suitable excipients are disclosed, for example, in texts such as *Remington's Pharmaceutical Manufacturing*, 13 Ed., Mack Publishing Co., Easton, Pa. (1965).

The following examples represent typical syntheses of the compounds as described by Schemes I and II. These examples are illustrative only and are not intended to limit the invention in any way. The reagents and starting materials are readily available to one of ordinary skill in the art. As used in the following examples, the following terms have the meanings indicated: "eq." refers to equivalents, "g" refers to grams, "mg" refers to milligrams, "mmol" refers to millimoles, "ml" refers to milliliters, "°C." refers to degrees Celsius, "TLC" refers to thin layer chromatography, "$R_f$" refers to retention factor and "δ" refers to parts per million downfield from tetramethylsilane.

EXAMPLE 1

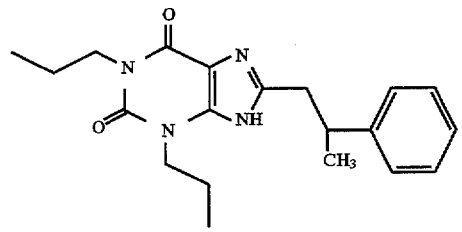

Preparation of 8-(2-Phenylpropyl)-1,3-dipropyl-3,9-dihydropurine-2,6-dione 1,3-Di-n-propyl-6-aminouracil (30 g) was suspended in 1 L of water with 41 ml of 20% acetic acid and overhead stirring. Sodium nitrite (9.03 g) in 41 ml of water was added in portions, keeping the solution acidic with 12 ml of concentrated hydrochloric acid. A purple precipitate formed. Addition was complete in 10 minutes and the suspension was allowed to stir for 2 hours. The solution was then filtered, and the filtrate was rinsed with water and dried under vacuum to yield 46 g of 1,3-di-n-propyl-5-nitroso-6-aminouracil.

The 1,3-di-n-propyl-5-nitroso-6-aminouracil (61.6 g) was suspended in 1 L of water, and the suspension was made alkaline to pH 11 with 50% ammonium hydroxide and treated with 100 g of sodium dithionite, in portions, until the purple color faded. The aqueous mixture was extracted with chloroform (8×200 ml), dried over magnesium sulfate, filtered and concentrated. The residue was purified by flash chromatography (5/10% methanol/chloroform) and recrystallized from 10% isopropanol in hexane and recrystallized from 10% isopropanol to yield 37.29 g of 1,3-di-n-propyl-5,6-diaminouracil, m.p., 127°–128° C.

Dissolve 3-phenylbutyric acid (1.0 g, 6.1 mmol) in tetrahydrofuran (20 ml), treat with N-methylmorpholine (0.67 ml, 6.1 mmol) and cool to −20° C. Add isobutyl chloroformate (0.79 ml, 6.1 mmol) and stir for 20 minutes. Then add 1,3-di-n-propyl-5,6-diaminouracil (1.4 g, 6.1 mmol, in 5 ml dimethylformamide) and stir the reaction at −20° C. for 3 hours. Then dilute the reaction with diethyl ether (400 ml) and separate the layers. Rinse the organic layer with saturated sodium bicarbonate (200 ml), 50% aqueous sodium chloride (2×200 ml), dry over anhydrous magnesium sulfate, filter and concentrate under vacuum to provide N-(2-amino-4,6-dioxo-3,5-dipropylcyclohex-1-enyl)-3-phenylbutyramide (2.23 g).

Dissolve N-(2-amino-4,6-dioxo-3,5-dipropyl-cyclohex-1-enyl)-3-phenylbutyramide (2.23 g, 6.2 mmol) in ethanol (100 ml), treat with 15% potassium hydroxide (100 ml) and heat to 60° C. for 3 hours. After cooling, acidify the reaction with concentrated hydrochloric acid (22 ml). Extract the reaction with diethyl ether (500 ml). Rinse the organic with water (200 ml), saturated sodium chloride solution (200 ml), dry over anhydrous magnesium sulfate, filter and concentrate under vacuum. Triturate the residue with 10% diethyl ether/hexane. Collect the solid and purify by radial chromatography (50% ethyl acetate/hexane, 4 mm plate) to provide the title compound (180 mg), m.p. 136°–137° C.
Anal Calcd for $C_{20}H_{26}N_4O_2$: C,67.77; H, 7.39; N, 15.81. Found: C, 67.66; H, 7.39; N, 15.74.

EXAMPLE 2

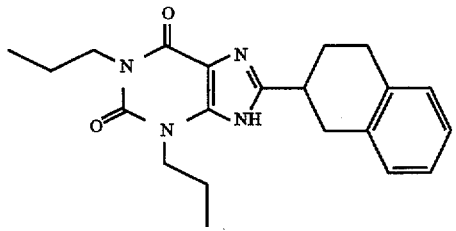

Preparation of 1,3-Dipropyl-8-(1,2,3,4-tetrahydronaphthalen-2-yl)-3,9-dihydropurine-2,6-dione Dissolve 1,2,3,4-tetrahydro-2-naphthoic acid (1.0 g, 5.67 mmol) in tetrahydrofuran (40 ml). Add N-methylmorpholine (0.62 ml, 5.67 mmol) and cool to −20° C. Add isobutyl chloroformate (0.73 ml, 5.67 mmol) and stir for 25 minutes. Then add 1,3-di-n-propyl-5,6-diaminouracil (1.28 g, 5.67 mmol, in 5 ml dimethylformamide) and stir the reaction for 5 hours at −20° C. Warm the reaction to room temperature and dilute with diethyl ether (300 ml). Separate the layers and rinse the organic layer with saturated sodium bicarbonate (200 ml), saturated sodium chloride solution (200 ml), dry over anhydrous magnesium sulfate, filter and concentrate. Purify the residue by radial chromatography (2% to 4% to 6% methanol/chloroform, 4 mm plate) to provide 1,2,3,4-tetrahydronaphthalene-2-carboxylic acid (2-amino-4,6-dioxo-3,5-dipropylcyclohex-1-enyl)amide (2.0 g) as a foam.

Dissolve 1,2,3,4-tetrahydronaphthalene-2-carboxylic acid (2-amino-4,6-dioxo-3,5-dipropylcyclohex-1-enyl)amide (2.0 g, 5.2 mmol) in ethanol (50 ml), add 15% potassium hydroxide (50 ml) and heat to 70° C. for 4 hours. After cooling to 0° C., acidify the reaction with concentrated hydrochloric acid (13 ml). Add water (100 ml) and collect the resulting precipitate by suction filtration. Purify the white solid by flash chromatography (50% ethyl acetate/hexane) and triturate with 5% diethyl ether/hexane to provide, after drying under vacuum at 120° C. for 30 minutes the title compound (1.04 g), m.p. 202°–204° C.
Anal Calcd for $C_{21}H_{26}N_4O_2$: C, 68.83; H, 7.15; N, 15.29. Found: C, 68.72; H, 7.11; N, 15.30.

EXAMPLE 3

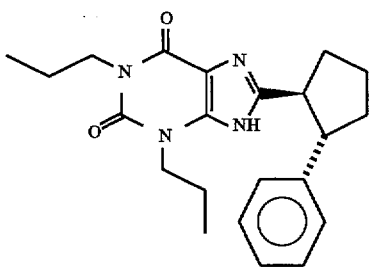

Preparation of 8-(trans-2-Phenylcyclopentyl)-1,3-dipropyl-3,9-dihydropurine-2,6-dione 1,3-Diallyl-6-aminouracil (5 g) was suspended in 400 ml of water in a one-liter round bottom flask with overhead stirring. Acetic acid (6.7 ml of a 20% solution) was added, followed by intermittent addition of 2 ml of concentrated hydrochloric acid and a sodium nitrite solution (1.53 g in 7 ml water). After 4 hours, this solution was filtered, washed with water, collected and dried in a vacuum oven at 80° C. for 20 hours to yield 4.54 g of 1,3-diallyl-5-nitroso-6-aminouracil as a purple solid, m.p. 170°–180° C. (87% yield).

The 1,3-diallyl-5-nitroso-6-aminouracil (4.5 g) was suspended in 150 ml of ethyl acetate and treated with 23.6 g of sodium dithionite in 64 ml of water. After 1 hour, the layers were separated and the aqueous phase was extracted with ethyl acetate (4×100 ml). The combined organic extracts were dried over magnesium sulfate, filtered and concentrated and the residue was purified by flash chromatography (10% methanol in chloroform) to yield 4.41 g of 1,3-diallyl-5,6-diaminouracil.

Dissolve trans-2-phenyl-cyclopentanecarboxylic acid (1.0 g, 5.3 mmol), prepared according to F. G. Bordwell and J. Almy, *J. Org. Chem.*, 38, 571 (1973), in tetrahydrofuran (20 ml) and add N-methylmorpholine (0.58 ml, 5.3 mmol). Cool the reaction to −20° C. and add isobutyl chloroformate (0.69 ml, 5.3 mmol). Stir the reaction for 30 minutes, add 1,3-diallyl-5,6-diaminouracil (1.2 g, 5.3 mmol, in 4 ml dimethylformamide) and stir at −20° C. for 3 hours. Warm to room temperature and dilute the reaction with diethyl ether (400 ml). Separate the layers and rinse the organic layer with saturated sodium bicarbonate (2×200 ml), 50% aqueous sodium chloride (2×300 ml), dry over anhydrous magnesium sulfate, filter and concentrate under vacuum. Purify the residue by radial chromatography (2% to 5% methanol/chloroform, 2 mm plate) to provide trans-2-phenyl-cyclo-pentanecarboxylic acid (3,5-diallyl-2-amino-4,6-dioxo-cyclohex-1-enylamide (0.51 g).

Dissolve trans-2-phenylcyclopentanecarboxylic acid (3,5-diallyl-2-amino-4,6-dioxo-cyclohex-1-enyl)amide (300 mg, 0.76 mmol) in ethanol (100 ml), add 10% potassium hydroxide (100 ml) and heat the reaction to 60° C. for 4 hours. Cool the reaction and dilute with water (200 ml). Acidify with concentrated hydrochloric acid and extract with diethyl ether (400 ml). Rinse the organic extract with water (200 ml), saturated sodium chloride (200 ml), dry over anhydrous magnesium sulfate, filter and concentrate under vacuum. Purify the residue by radial chromatography (40% to 50% ethyl acetate/hexane, 2 mm plate) to provide 5,7-diallyl-2-(2-phenylcyclopentyl)-1,7-dihydrobenzoimidazole-4,6-dione (149 mg).

Dissolve 5,7-diallyl-2-(2-phenylcyclopentyl)-1,7-dihydrobenzoimidazole-4,6-dione (139 mg, 0.37 mmol) in methanol (20 ml). Add a catalytic amount of 10% palladium/ carbon and place under an atmosphere of hydrogen with stirring. After 45 minutes when hydrogenation is complete, purge the reaction with nitrogen and filter through diatomaceous earth. Concentrate the filtrate under vacuum and purify the residue by radial chromatography (40% to 50% ethyl acetate/hexane, 2 mm plate) to provide the title compound (98 mg), m.p. 152°–153° C.

Anal Calcd for $C_{22}H_{28}N_4O_2$: C, 69.45; H, 7.42; N, 14.72. Found: C, 69.36; H, 7.56; N, 14.63.

What is claimed is:

1. A compound which is 1,3-dipropyl-8-(1,2,3,4-tetrahydronaphthalen-2-yl)-3,9-dihydro-purine-2,6-dione.

* * * * *